(12) United States Patent
Rossi

(10) Patent No.: US 7,866,203 B2
(45) Date of Patent: Jan. 11, 2011

(54) METHOD FOR THE QUANTITATIVE DETERMINATION OF POLOXAMERS

(75) Inventor: Mara Rossi, Rome (IT)

(73) Assignee: Ares Trading S.A., Aubonne (CH)

(*) Notice: Subject to any disclaimer, the term of this patent is extended or adjusted under 35 U.S.C. 154(b) by 332 days.

(21) Appl. No.: 12/066,799

(22) PCT Filed: Sep. 14, 2006

(86) PCT No.: PCT/EP2006/066383
§ 371 (c)(1), (2), (4) Date: Mar. 13, 2008

(87) PCT Pub. No.: WO2007/031566
PCT Pub. Date: Mar. 22, 2007

(65) Prior Publication Data
US 2008/0190179 A1    Aug. 14, 2008

Related U.S. Application Data

(60) Provisional application No. 60/717,642, filed on Sep. 16, 2005.

(30) Foreign Application Priority Data
Sep. 14, 2005    (EP) ................... 05108439

(51) Int. Cl.
G01N 30/00    (2006.01)
(52) U.S. Cl. .................................. 73/61.52
(58) Field of Classification Search ........... 73/61.52
See application file for complete search history.

(56) References Cited

U.S. PATENT DOCUMENTS

| | | | |
|---|---|---|---|
| 3,119,740 A | 1/1964 | Steelman et al. | |
| 4,886,750 A * | 12/1989 | Bertola et al. | 435/136 |
| 5,037,751 A * | 8/1991 | Bertola et al. | 435/197 |
| 5,767,067 A | 6/1998 | Arpaia et al. | |
| 5,981,568 A * | 11/1999 | Kunz et al. | 514/411 |
| 6,306,421 B1 * | 10/2001 | Kunz et al. | 424/423 |
| 6,358,989 B1 * | 3/2002 | Kunz et al. | 514/411 |
| 6,433,144 B1 * | 8/2002 | Morris et al. | 530/351 |
| 6,491,938 B2 * | 12/2002 | Kunz et al. | 424/423 |
| 6,569,441 B2 * | 5/2003 | Kunz et al. | 424/423 |
| 6,663,881 B2 * | 12/2003 | Kunz et al. | 424/423 |
| 6,720,350 B2 * | 4/2004 | Kunz et al. | 514/411 |

(Continued)

FOREIGN PATENT DOCUMENTS

WO    WO 91/09955    7/1991

(Continued)

OTHER PUBLICATIONS

Cerpa-Poljak, A. et al. "Isoelectric Charge of Recombinant Human Follicle-Stimulating Hormone Isoforms Determines Receptor Affinity and in Vitro Bioactivity" *Endocrinology*, 1993, pp. 351-356, vol. 132, No. 1.

(Continued)

*Primary Examiner*—David A. Rogers
*Assistant Examiner*—Rodney T Frank
(74) *Attorney, Agent, or Firm*—Saliwanchik, Lloyd & Saliwanchik (57) ABSTRACT

The invention relates to the analytical determination of poloxamers in a liquid protein sample.

16 Claims, 1 Drawing Sheet

U.S. PATENT DOCUMENTS

| | | | |
|---|---|---|---|
| 7,125,843 B2 * | 10/2006 | DeFrees et al. | 514/8 |
| 7,157,277 B2 * | 1/2007 | DeFrees et al. | 435/351 |
| 7,164,005 B2 * | 1/2007 | Costantino et al. | 530/350 |
| 7,173,003 B2 * | 2/2007 | DeFrees et al. | 514/8 |
| 7,179,617 B2 * | 2/2007 | DeFrees et al. | 435/68.1 |
| 7,214,660 B2 * | 5/2007 | DeFrees et al. | 514/8 |
| 7,226,903 B2 * | 6/2007 | DeFrees et al. | 514/8 |
| 7,265,084 B2 * | 9/2007 | DeFrees et al. | 514/6 |
| 7,265,085 B2 * | 9/2007 | DeFrees et al. | 514/8 |
| 7,297,511 B2 * | 11/2007 | DeFrees et al. | 435/68.1 |
| 7,399,613 B2 * | 7/2008 | DeFrees et al. | 435/89 |
| 7,462,365 B2 * | 12/2008 | Costantino et al. | 424/468 |
| 2001/0014326 A1 * | 8/2001 | Andya et al. | 424/130.1 |
| 2003/0202972 A1 * | 10/2003 | Andya et al. | 424/131.1 |
| 2007/0072303 A1 * | 3/2007 | Arpaia et al. | 436/86 |

FOREIGN PATENT DOCUMENTS

| | | |
|---|---|---|
| WO | WO 98/58957 | 12/1998 |
| WO | WO 01/58493 | 8/2001 |
| WO | WO 2004/087213 | 10/2004 |
| WO | WO 2004/104025 | 12/2004 |

OTHER PUBLICATIONS

Dias, J.A. et al. "Receptor Binding and Functional Properties of Chimeric Human Follitropin Prepared by an Exchange between a Small Hydrophilic Intercysteine Loop of Human Follitropin and Human Lutropin" *The Journal of Biological Chemistry*, Oct. 14, 1994, pp. 25289-25294, vol. 269, No. 41.

Flack, M.R. et al. "Site-directed Mutagenesis Defines the Individual Roles of the Glycosylation Sites on Follicle-stimulating Hormone" *The Journal of Biological Chemistry*, May 13, 1994, pp. 14015-14020, vol. 269, No. 19.

Hakola, K. et al. "Recombinant rat follicle-stimulating hormone; production by Chinese hamster ovary cells, purification and functional characterization" *Molecular and Cellular Endocrinology*, 1997, pp. 59-69, vol. 127.

Jewell, R.C. et al. "Pharmacokinetics of RheothRx Injection in Healthy Male Volunteers" *Journal of Pharmaceutical Sciences*, Jul. 1997, pp. 808-812, vol. 86, No. 7.

Katakam, M. et al. "Effect of Surfactants on the Physical Stability of Recombinant Human Growth Hormone" *Journal of Pharmaceutical Sciences*, Jun. 1995, pp. 713-716, vol. 84, No. 6.

Keene, J.L. et al. "Expression of Biologically Active Human Follitropin in Chinese Hamster Ovary Cells" *The Journal of Biological Chemistry*, Mar. 25, 1989, pp. 4769-4775, vol. 264, No. 9.

Klein, J.K. et al. "Pharmacokinetics and pharmacodynamics of single-chain recombinant human follicle-stimulating hormone containing the human chorionic gonadotropin carboxyterminal peptide in the rhesus monkey" *Fertility and Sterility*, Jun. 2002, pp. 1248-1255, vol. 77, No. 6.

Klein, J. et al. "Development and characterization of a long-acting recombinant hFSH agonist" *Human Reproduction*, 2003, pp. 50-56, vol. 18, No. 1.

Lapolt, P.S. et al. "Enhanced Stimulation of Follicle Maturation and Ovulatory Potential by Long Acting Follicle-Stimulating Hormone Agonists with Extended Carboxyl-Terminal Peptides" *Endocrinology*, 1992, pp. 2514-2520, vol. 131, No. 6.

Mao, Y. et al. "Quantitation of poloxamers in pharmaceutical formulations using size exclusion chromatography and colorimetric methods" *Journal of Pharmaceutical and Biomedical Analysis*, 2004, pp. 1127-1142, vol. 35.

Moghimi, S.M. et al. "Causative factors behind poloxamer 188 (Pluronic F68, Flocor™)-induced complement activation in human sera. A protective role against poloxamer-mediated complement activation by elevated serum lipoprotein levels" *Biochimica et Biophysica Acta*, 2004, pp. 103-113, vol. 1689.

Valove, F.M. et al. "Receptor Binding and Signal Transduction Are Dissociable Functions Requiring Different Sites on Follicle-Stimulating Hormone" *Endocrinology*, 1994, pp. 2657-2661, vol. 135, No. 6.

* cited by examiner

Figure 1

METHOD FOR THE QUANTITATIVE DETERMINATION OF POLOXAMERS

CROSS-REFERENCE TO RELATED APPLICATION

This application is the U.S. national stage application of International Patent Application No. PCT/EP2006/066383, filed Sep. 14, 2006, which claims the benefit of U.S. Provisional Patent Application No. 60/717,642, filed Sep. 16, 2005, the disclosures of which are hereby incorporated by reference in their entireties, including all figures, tables and amino acid or nucleic acid sequences.

FIELD OF INVENTION

The invention relates to the field of the analytical determination of a surfactant belonging to the class of poloxamers in a liquid protein sample.

BACKGROUND OF THE INVENTION

Poloxamers are non-ionic block copolymers of ethylene oxide (EO) and propylene oxide (PO). They are used in pharmaceutical formulations as surfactants, emulsifying agents, solubilisation agents and dispersing agents.

A well known analytical approach for characterising a poloxamer is a calorimetric method in which the UV absorbance at 320 and 620 nm, resulting from complex formation of the poloxamer with cobalt (II) thiocyanate, is analysed.

Yun Mao et al (*Journal of Pharmaceutical and Biomedical Analysis*, 35 (2004), 1127) describe for poloxamer determination the use of size exclusion chromatography (SEC) using a column with THF as mobile phase and refractive index (RI) detection. The method was applied to the pharmaceutical formulations Avapro, Neurontin and Sudafed wherein the active principle is a "small molecule". Small molecules are conveniently separable by SEC from the high molecular mass poloxamers.

Size-exclusion chromatography (SEC), also called gel-permeation chromatography (GPC), uses porous particles to separate molecules of different sizes. It is generally used to separate polymer molecules and to determine molecular weights and molecular weight distributions of polymers. Molecules that are smaller than the pore size can enter the particles and therefore have a longer path and longer transit time than larger molecules that cannot enter the particles. All molecules larger than the pore size are unretained and elute together. Molecules that can enter the pores will have an average residence time in the particles that depends on the molecules size and shape. Different molecules therefore have different total transit times through the column.

No method has been provided so far allowing the quantitative determination of poloxamers in protein samples, wherein the protein has a molecular mass which is comparable to the poloxamers.

There is in particular a need for the quantitative determination of poloxamers in protein samples, wherein the protein has a molecular mass between 5 to 70 kDa, preferably between 20 to 70 kDa.

SUMMARY OF THE INVENTION

The present invention relates to a method allowing the quantitative determination of a poloxamer in a protein sample, in particular a liquid protein sample, e.g. in a liquid pharmaceutical formulation. In particular, the invention provides a method for the quantitative measurement of the poloxamer concentration in a protein sample. Thus, at any time during the shelf life of about 2 years of a protein formulation, the poloxamer amount in the formulation can be determined.

The method for the quantitative determination of a poloxamer in a liquid protein sample comprises the steps of subjecting said sample to:
(a) a separation step of the ingredients of said sample using a size exclusion chromatography column; and
(b) a detection step of the poloxamer by analyzing the refractory index;

Preferably, the present invention relates to a method for the quantitative determination of a poloxamer in a liquid protein sample comprising the steps of subjecting said sample to:
(a) a separation step using a size exclusion chromatography column;
(b) an elution step with a mobile phase;and
(c) optionally a detection step for the poloxamer.

Thus the size exclusion chromatography combined with an elution step with a mobile phase allows to separate the poloxamer from the remaining ingredients.

The poloxamer is detected in the context of a further step by analysing the eluted phase, for example using a RI (refractory index) detection system.

BRIEF DESCRIPTION OF THE DRAWING

FIG. 1 shows a chromatogram for the quantitative determination of Poloxamer 188 in a hCG formulation. The Poloxamer 188 peak area is in this example at an elution time of about 14-16 minutes (the retention time may vary as a function of the flow rate). The area under the curve allows the quantification of the Poloxamer 188 within the hCG sample.

ABBREVIATIONS

The following abbreviations are used in the description of the invention:
FSH: follicle stimulating hormone;
r-FSH; r-LH; r-hCG; r-GH; r-IFN beta, r-TSH: recombinant FSH, LH, hCG, GH, INF beta, TSH;
hFSH: human FSH;
r-hFSH: recombinant human FSH
RI: Refractive Index
KD or Kd or kDa: kiloDalton
SEC: Size Exclusion Chromatography
RT: Room Temperature
WFI: water for injection
Poloxamer 188: synonym of Pluronic F68 of BASF Inc.

DETAILED DESCRIPTION OF THE INVENTION

The present invention relates to a convenient method allowing the quantitative determination of a poloxamer—which is a surfactant—in a protein sample. Preferably, the protein sample is a liquid protein sample. The liquid protein sample may be in the form of any liquid formulation, preferably it is a liquid pharmaceutical formulation as described below. In one embodiment, said liquid pharmaceutical protein sample is contained in a vial, either for single or multi-dose administration.

In a further embodiment the protein sample to be analysed is freeze dried and is to be solubilized in a suitable aqueous solvent prior to be analysed.

The method for the quantitative determination of a poloxamer in a liquid protein sample comprises the steps of subjecting said sample to:

(a) a separation step of the ingredients of said sample using a size exclusion chromatography column (in particular a SE-HPLC column); and (b) a detection step of the poloxamer by analyzing the refractory index.

Preferably, the invention provides a method for the quantitative determination of a poloxamer in a liquid protein sample comprising the steps of subjecting said sample to:

(a) a separation step using a size exclusion chromatography column;

(b) an elution step with a mobile phase;and (c) optionally a detection step for the poloxamer.

Typically the size exclusion column would be a SE-HPLC column.

In one embodiment, the poloxamer is Poloxamer 188.

In a preferred embodiment the protein in the liquid protein sample has a molecular mass which is comparable to the poloxamer mass.

In a particularly preferred embodiment, the protein in the liquid protein sample has a molecular mass between 5 to 70 kDa, more preferably between 20 to 70 kDa.

The ratio of the protein mass to the respective poloxamer mass may preferably be between 1:3 and 10:1, preferably between 1:2 and 7:1.

Examples of proteins according to the present invention include mammalian proteins, such as, e.g., growth hormone, including human growth hormone and bovine growth hormone; growth hormone releasing factor; parathyroid hormone; thyroid stimulating hormone; lipoproteins; a-I-antitrypsin; insulin A-chain; insulin B-chain; proinsulin; follicle stimulating hormone; choriogonadotropin; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such asurokinase or tissue-type plasminogen activator (t-PA); bombazine; thrombin; tumor necrosis factor-alpha and -beta; enkephalinase; RANTES (regulated on activation normally T-cell expressed and secreted); human macrophage inflammatory protein(MIP-I-alpha); serum albumin such as human serum albumin; mullerian-inhibiting substance; relaxin A-chain; relaxin B-chain; prorelaxin; mouse gonadotropin-associated peptide; Dnase; inhibin; activin; vascular endothelial growth factor (VEGF); receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-P; platelet-derived growth factor (PDGF); fibroblast growth factor such as aFGF and bFGF, in particular FGF-18; epidermal growth factor (EGF); transforming growth factor (TGF) such as TGF-alpha and TGF-beta, including TGF-beta1, TGF-beta2, TGF-beta3, TGF-beta4, or TGF-beta5; insulin-like growth factor I and-II (IGF-I and IGF-II);des(I-3)-IGF-1 (brain IGF-I); insulin-like growth factor binding proteins; CD proteins such as CD3, CD4, CD8, CD19 and CD20; erythropoietin (EPO); thrombopoietin (TPO); osteoinductive factors; osteopontin; immunotoxins; a bone morphogenetic protein (BMP); an interferon such as interferon-alpha,-beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor (DAF); a viral antigen such as, for example, a portion of the AIDS envelope; transport proteins; homing receptors; addressins; regulatory proteins; immunoadhesins; antibodies; and biologically active fragments or variants of any of the above-listed polypeptides.

Preferably, the protein according to the present invention is selected from follicle stimulating hormone (FSH), choriogonadotropin (CG), luteinizing hormone (LH), Interferon beta (IFN-beta), pegylated Interferon beta (PEG-IFN-beta), growth hormone (GH), thyroid stimulating hormone (TSH), fibroblast growth factor 18 (FGF-18) or osteopontin.

FSH, CG, LH and TSH are glycoproteins falling into the class of gonadotrophins. Gonadotrophins are used in the treatment of infertility.

IFN-beta is a glycoprotein falling into the class of interleukins. IFN-beta is used in the treatment of multiple sclerosis.

PEG-IFN-beta is an IFN-beta derivatized by a polyethylene glycol chain, which confers improved stability.

Growth hormone is a non-glycosylated protein. It is used to treat child or adult growth hormone deficiencies.

FGF-18 is used in the treatment of osteoarthritis.

Osteopontin is a glycosylated single chain polypeptide.

In one preferred embodiment said protein is a heterodimer such as the gonadotropins (FSH, LH, CG, TSH as well as variants). In a further embodiment the protein is Growth Hormone (GH) or interferon beta (IFN-beta or variants, e.g. pegylated variants). In a still further embodiment, the protein is FGF-18 or osteopontin.

In a preferred embodiment, the liquid protein sample includes one or more therapeutic proteins. Preferably, such sample does not include a non-protein therapeutic, such as a small molecular weight chemical compound.

Follicle stimulating hormone, or FSH, as used herein refers to the FSH produced as a full-length mature protein which includes, but is not limited to human FSH or "hFSH", whether produced recombinantly or isolated from human sources, such as the urine of postmenopausal women.

The method is applicable to natural as well as recombinant proteins. In one embodiment the protein formulation is human recombinant FSH, LH, CG, TSH, GH or IFN-beta.

Follicle-stimulating hormone (FSH) is a glycoprotein falling into the class of gonadotrophins. FSH is used in the treatment of infertility and reproductive disorders in both female and male patients, e.g. to induce spermatogenesis in men suffering from oligospermia.

Luteinising Hormone (LH) is a gonadotropin secreted by the anterior lobe of the pituitary. LH is used in female patients in combination with FSH in OI (ovulation induction) and in COH (controlled ovarian hyperstimulation), particularly in those patients having very low endogenous LH levels or resistance to LH, such as women suffering from hypogonadotrophic hypogonadism (HH, WHO group I) or older patients (i.e. 35 years or older), and patients in which embryo implantation or early miscarriage is a problem.

Chorionic gonadotropin (CG) is a gonadotropin produced by the placenta and obtained from the urine of pregnant women. CG acts at the same receptor as LH and elicits the same responses. CG has a longer circulation half-life than LH and is therefore commonly used as a long-acting source of LH-activity. CG is used in QI and COH regimens to mimic the natural LH peak and trigger ovulation. An injection of human chorionic gonadotrophin (hCG) is used to trigger ovulation at the end of stimulation with FSH or a mixture of FSH and LH. CG may also be used together with FSH during stimulation for QI and COH, in order to provide LH-activity during stimulation in patients in which LH-activity is desirable, such as those mentioned above.

FSH, LH and CG are members of the heterodimer, glycoprotein hormone family that also includes thyroid stimulating hormone (TSH). The members of this family are heterodimers, comprising an α- and a β-subunit. The subunits are held together by noncovalent interactions. The human FSH (hFSH) heterodimer consists of (i) a mature 92 amino acid glycoprotein alpha subunit, which also is common to the other human family members (i.e. chorionic gonadotrophin ("CG"), luteinising hormone ("LH") and thyroid stimulating hormone ("TSH"); and (ii) a mature 111 amino acid beta subunit that is unique to FSH. The human LH heterodimer consists of (i) the mature 92 amino acid glycoprotein alpha subunit; and (ii) a mature 112 beta subunit that is unique to LH. The alpha and beta subunits of the glycoproteins may be prone to dissociate in formulations, due to interaction with a preservative, surfactant and other excipients. Dissociation of the subunits leads to loss of biological potency.

FSH is formulated for intramuscular (IM) or subcutaneous (SC) injection. In one embodiment FSH is supplied in lyophilised (solid) form in vials or ampoules of 75 IU/vial and 150 IU/vial with a shelf life of one and a half to two years when stored at 2-25° C. A solution for injection is formed by reconstituting the lyophilised product with water for injection (WFI). Furthermore, a liquid FSH formulations is available (Gonal-F pen) containing 22 µg/0.5 ml, 33 µg/075 ml or 66 µg/1.5 ml of FSH as well as Poloxamer 188, saccharose, buffer, methionine and m-cresol.

Hence, FSH has been formulated in both single-dose and multi-dose liquid formats, in vials, or ampoules. Single dose formats must remain stable and potent in storage prior to use. Multi-dose formats must not only remain stable and potent in storage prior to use, but must also remain stable, potent and relatively free of bacteria over the multiple-dose use regimen administration period, after the seal of the ampoule has been compromised. For this reason, multi-dose formats usually contain a bacteriostatic agent, e.g. benzyl alcohol or m-cresol.

LH is formulated for intramuscular (IM) or subcutaneous (SC) injection. LH is supplied in lyophilised (solid) form in vials or ampoules of 75 IU/vial with a shelf life of one and a half to two years when stored at 2-25° C. A solution for injection is formed by reconstituting the lyophilised product with water for injection (WFI). Luveris™ contains further to LH the following excipients: saccharose, buffer, Polysorbat 20, methionine. More recently, LH formulations were described containing Poloxamer 188 (WO 2004/087213).

Liquid pharmaceutical compositions containing hCG are also on the market e.g. Ovitrelle™ containing mannitol, in a phosphate buffer at pH 7, methionine, Poloxamer 188.

The expression "variant" is meant to encompass those molecules differing in amino acid sequence, glycosylation pattern or in inter-subunit linkage from human FSH, LH, CG, TSH, IFN-beta or GH but are exhibiting the corresponding biological activity of FSH, LH, CG, TSH, IFN-beta or GH. Examples include CTP-FSH, a long-acting modified recombinant FSH, consisting of the wild type α-subunit and a hybrid β-subunit in which the carboxy terminal peptide of hCG has been fused to the C-terminal of the β-subunit of FSH, as described in LaPolt et al.; Endocrinology; 1992, 131, 2514-2520; or Klein et al.; Development and characterization of a long-acting r-hFSH agonist; Human Reprod. 2003,18, 50-56]. Also included is single chain CTP-FSH, a single chain molecule, consisting of the following sequences (from N-terminal to C-terminal):

| βFSH | βhCG-CTP(113-145) | αFSH |
|---|---|---| wherein βFSH signifies the β-subunit of FSH, βhCG CTP (113-145) signifies the carboxy terminal peptide of hCG and αFSH signifies the α-subunit of FSH, as described by Klein et al.; (*Pharmacokinetics and pharmacodynamics of single-chain recombinant human follicle-stimulating hormone containing the human chorionic gonadotrophin carboxyterminal peptide in the rhesus monkey; Fertility & Sterility;* 2002, 77, 1248-1255). Other examples of FSH variants include FSH molecules having additional glycosylation sites incorporated in the α- and/or β-subunit, as disclosed in WO 01/58493 (Maxygen), particularly as disclosed in claims 10 and 11 of WO 01/58493, and FSH molecules with intersubunit S—S bonds, as disclosed in WO 98/58957.

The FSH variants referred to herein also include the carboxy terminal deletions of the beta subunit that are shorter than the full length mature FSH protein. FSH heterodimers or FSH variant heterodimers can be produced by any suitable method, such as recombinantly, by isolation or purification from natural sources as may be the case, or by chemical synthesis, or any combination thereof.

"Variants" also comprises pegylated forms of the proteins.

The use of the term "recombinant" refers to preparations of FSH, LH, CG, TSH, GH, IFN beta or variants that are produced through the use of recombinant DNA technology (see for example WO 85/01958). One example of a method of expressing FSH or LH using recombinant technology is by transfection of eukaryotic cells with the DNA sequences encoding an alpha and beta subunit of FSH or LH, whether provided on one vector or on two vectors with each subunit having a separate promoter, as described in European patent nos. EP 0 211 894 and EP 0 487 512. Another example of the use of recombinant technology to produce FSH or LH is by the use of homologous recombination to insert a heterologous regulatory segment in operative connection to endogenous sequences encoding the subunits of FSH or LH, as described in European patent no. EP 0 505 500 (Applied Research Systems ARS Holding NV).

The FSH or FSH variant used in accordance with the present invention may be produced not only by recombinant means, including from mammalian cells, but also may be purified from other biological sources, such as from urinary sources. Acceptable methodologies include those described in Hakola, K. Molecular and Cellular Endocrinology, 127:59-69, 1997; Keene, et al., J. Biol. Chem., 264 :4769-4775, 1989; Cerpa-Poljak, et al., Endocrinology, 132: 351-356, 1993; Dias, et al., J. Biol. Chem., 269:25289-25294, 1994; Flack, et al., J. Biol. Chem., 269:14015-14020, 1994; and Valove, et al., Endocrinology, 135:2657-2661, 1994, U.S. Pat. No. 3,119,740 and U.S. Pat. No. 5,767,067.

Luteinising hormone, or LH, as used herein refers to the LH produced as a full-length mature protein, which includes, but is not limited to human LH, whether produced recombinantly or isolated from human sources, such as the urine of postmenopausal women. The protein sequence of the human glycoprotein alpha subunit is provided in SEQ ID NO: 1, and the protein sequence of the human LH beta subunit is given in SEQ ID NO: 6. In a preferred embodiment the LH is recombinant.

The expression "LH variant" is meant to encompass those molecules differing in amino acid sequence, glycosylation pattern or in inter-subunit linkage from human LH but exhibiting LH-activity.

LH heterodimers or LH variant heterodimers can be produced by any suitable method, such as recombinantly, by isolation or purification from natural sources as may be the case, or by chemical synthesis, or any combination thereof.

The liquid protein samples of the present invention also comprise mixtures of FSH /LH and variants (WO 2004/087213) as well as FSH and hCG and variants (WO 2004/105788)

The term "aqueous diluent" refers to a liquid solvent that contains water. Aqueous solvent systems may be consist solely of water, or may consist of water plus one or more miscible solvents, and may contain dissolved solutes such as sugars, buffers, salts or other excipients. The more commonly used non-aqueous solvents are the short-chain organic alcohols, such as, methanol, ethanol, propanol, short-chain ketones, such as acetone, and poly alcohols, such as glycerol.

The term "bacteriostatic" or "bacteriostatic agent" refers to a compound or compositions added to a formulation to act as an anti-bacterial agent. A preserved FSH or FSH variant or FSH and LH containing formulation of the present invention preferably meets statutory or regulatory guidelines for preservative effectiveness to be a commercially viable multi-use product, preferably in humans. Examples of bacteriostatics include phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal.

The term "buffer" or "physiologically-acceptable buffer" refers to solutions of compounds that are known to be safe for pharmaceutical or veterinary use in formulations and that have the effect of maintaining or controlling the pH of the formulation in the pH range desired for the formulation. Acceptable buffers for controlling pH at a moderately acidic pH to a moderately basic pH include, but are not limited to, such compounds as phosphate, acetate, citrate, arginine, TRIS, and histidine. "TRIS" refers to 2-amino-2-hydroxymethyl-1,3,-propanediol, and to any pharmacologically acceptable salt thereof. Preferable buffers are phosphate buffers with saline or an acceptable salt.

The term "phosphate buffer" refers to solutions containing phosphoric acid or salts thereof, adjusted to a desired pH. Generally phosphate buffers are prepared from phosphoric acid, or a salt of phosphoric acid, including but not limited to sodium and potassium salts. Several salts of phosphoric acid are known in the art, such as sodium and potassium monobasic, dibasic, and tribasic salts of the acid. Salts of phosphoric acid are also known to occur as hydrates of the occurring salt. Phosphate buffers may cover a range of pHs, such as from about pH 4 to about pH 10, and preferred ranges from about pH 5 to about pH 9, and a most preferred range of at or about 6.0 to at or about 8.0, most preferably at or about pH 7.0.

The term "vial" refers broadly to a reservoir suitable for retaining FSH in solid or liquid form in a contained sterile state. Examples of a vial as used herein include ampoules, cartridges, blister packages, or other such reservoir suitable for delivery of the FSH to the patient via syringe, pump (including osmotic), catheter, transdermal patch, pulmonary or transmucosal spray. Vials suitable for packaging products for parenteral, pulmonary, transmucosal, or transdermal administration are well known and recognized in the art.

The expression "multi-dose use" is intended to include the use of a single vial, ampoule or cartridge of an FSH formulation or a formulation of the protein for more than one injection, for example 2, 3, 4, 5, 6 or more injections. The injections are preferably made over a period of at least at or about 12 hours, 24 hours, 48 hours, etc., preferably up to a period of at or about 12 days. The injections may be spaced in time, for example, by a period of 6, 12, 24, 48 or 72 hours.

The term "stability" refers to the physical, chemical, and conformational stability of the given protein in the formulations of the present invention (including maintenance of biological potency). Instability of a protein formulation may be caused by chemical degradation or aggregation of the protein molecules to form higher order polymers, by dissociation of the heterodimers into monomers, deglycosylation, modification of glycosylation, oxidation (particularly in heterodimers of the (α-subunit) or any other structural modification that reduces at least one biological activity of a polypeptide included in the present invention.

A "stable" solution or formulation, is one wherein the degree of degradation, modification, aggregation, loss of biological activity and the like, of the proteins therein is acceptably controlled, and does not increase unacceptably with time. Preferably the formulation retains at least at or about 80% of the labelled protein activity over a period of up to 2 years.

The problem underlying the present invention is to provide a convenient and rapid method for determining the amount of a poloxamer in a protein sample. A poloxamer can be used as a surfactant and is selected from block copolymers of ethylene oxide and propylene oxide, preferably Pluronic® F77, Pluronic F87, Pluronic F88 and Pluronic® F68, particularly preferably Pluronic F68 (BASF, Pluronic F68 is also known as Poloxamer 188).

As mentioned above, pharmaceutical formulations should have a shelf life of up to 2 years at a storage temperature of 2-25° C. This implies that the formulation is expected to remain stable during this time. Since liquid formulations contain various excipients that may affect directly or via decomposition indirectly the stability of the protein formulation, there is a need to have the analytical tools to assess said stability of the formulation.

More specifically, poloxamer surfactants are block copolymers of ethylene oxide (EO) and propylene oxide (PO). The propylene oxide block (PO) is sandwiched between two ethylene oxide (EO) blocks.

Poloxamers are synthesised in a two-step process:

A hydrophobe of the desired molecular weight is created by the controlled addition of propylene oxide to the two hydroxyl groups of propylene glycol; and Ethylene oxide is added to sandwich the hydrophobe between hydrophilic groups.

Poloxamer surfactants are also known as pluronics.

In Pluronic® F77, the percentage of polyoxyethylene (hydrophile) is 70%, and the molecular weight of the hydrophobe (polyoxypropylene) is approximately 2,306 Da.

In Pluronic F87, the percentage of polyoxyethylene (hydrophile) is 70%, and the molecular weight of the hydrophobe (polyoxypropylene) is approximately 2,644 Da.

In Pluronic F88, the percentage of polyoxyethylene (hydrophile) is 80%, and the molecular weight of the hydrophobe (polyoxypropylene) is approximately 2,644 Da.

In Pluronic F68, the percentage of polyoxyethylene (hydrophile) is 80%, and the molecular weight of the hydrophobe (polyoxypropylene) is approximately 1,967 Da.

Typical properties of Pluronic F77 are listed below:

Average Molecular Weight: 6600;

Melt/pour point: 48° C.;

Physical Form@20° C.: solid;

Viscosity (Brookfield) cps: 480 [liquids at 25° C., pastes at 60° C and solids at 77° C.];

Surface tension, dynes/cm@25° C.
0.1% Conc.: 47.0
0.01% Conc.: 49.3
0.001% Conc.: 52.8
Interfacial tension, dynes/cm@25° C. vs. Nujol;
0.1% Conc.: 17.7
0.01% Conc.: 20.8
0.01% Conc.: 25.5
Draves Wetting, Seconds 25° C.
1.0% Conc.: >360
0.1% Conc.: >360
Foam Height
Ross Miles, 0.1%, mm@50° C.: 100
Ross Miles, 0.1%, mm@26° C.: 47
Dynamic, 0.1%, mm@400 ml/min: >600
Cloud point in aqueous solution, ° C.
1% Conc.: >100
10% Conc.: >100
HLB (hydrophile-lipophile balance): 25
Typical properties of Pluronic F87 are listed below:
Average Molecular Weight: 7700;
Melt/pour point: 49° C.;
Physical Form@20° C.: solid;
Viscosity (Brookfield) cps: 700 [liquids at 25° C., pastes at 60° C. and solids at 77° C.];
Surface tension, dynes/cm@25° C.
0.1% Conc.: 44.0
0.01% Conc.: 47.0
0.001% Conc.: 50.2
Interfacial tension, dynes/cm@25° C. vs Nujol;
0.1% Conc.: 17.4
0.01% Conc.: 20.3
0.01% Conc.: 23.3
Draves Wetting, Seconds 25° C.
1.0% Conc.: >360
0.1% Conc.: >360
Foam Height
Ross Miles, 0.1%, mm@50° C.: 80
Ross Miles, 0.1%, mm@26° C.: 37
Dynamic, 0.1%, mm@400 ml/min: >600
Cloud point in aqueous solution, ° C.
1% Conc.: >100
10% Conc.: >100
HLB (hydrophile-lipophile balance): 24
Typical properties of Pluronic F88 are listed below:
Average Molecular Weight: 11400;
Melt/pour point: 54° C.;
Physical Form@20° C.: solid;
Viscosity (Brookfield) cps: 2300 [liquids at 25° C., pastes at 60° C. and solids at 77° C.];
Surface tension, dynes/cm@25° C.;
0.1% Conc.: 48.5
0.01% Conc.: 52.6
0.001% Conc.: 55.7
Interfacial tension, dynes/cm@25° C. vs Nujol;
0.1% Conc.: 20.5
0.01% Conc.: 23.3
0.01% Conc.: 27.0
Draves Wetting, Seconds 25° C.
1.0% Conc.: >360
0.1% Conc.: >360
Foam Height
Ross Miles, 0.1%, mm@50° C.: 80
Ross Miles, 0.1%, mm@26° C.: 37
Dynamic, 0.1%, mm@400 ml/min: >600
Cloud point in aqueous solution, ° C.
1% Conc.: >100
10% Conc.: >100
HLB (hydrophile-lipophile balance): 28
Typical properties of Pluronic F68 are listed below:
Average Molecular Weight: 8400;
Melt/pour point: 52° C.;
Physical Form@20° C.: solid;
Viscosity (Brookfield) cps: 1000 [liquids at 25° C., pastes at 60° C. and solids at 77° C.];
Surface tension, dynes/cm@25° C.
0.1% Conc.: 50.3
0.01% Conc.: 51.2
0.001% Conc.: 53.6
Interfacial tension, dynes/cm@25° C. vs Nujol;
0.1% Conc.: 19.8
0.01% Conc.: 24.0
0.01% Conc.: 26.0
Draves Wetting, Seconds 25° C.
1.0% Conc.: >360
0.1% Conc.: >360
Foam Height
Ross Miles, 0.1%, mm@50° C.: 35
Ross Miles, 0.1%, mm@26° C.: 40
Dynamic, 0.1%, mm@400 ml/min: >600
Cloud point in aqueous solution, ° C.
1% Conc.: >100
10% Conc.: >100
HLB (hydrophile-lipophile balance): 29

Other poloxamer polymers having properties similar to those listed above may also be used in the formulations of the invention. The preferred poloxamer surfactant present in the protein formulations that are analysed with the present method is Pluronic F68 (=Poloxamer 188).

Preferably the concentration of Pluronic, particularly Pluronic F68, in liquid protein formulations is at or about 0.01 mg/ml to at or about 1 mg/ml, more preferably at or about 0.05 mg/ml to at or about 0.5 mg/ml, more particularly preferably at or about 0.2 mg/ml to at or about 0.4 mg/ml, most preferably at or about 0.1 mg/ml.

The protein formulations analysed according to the method of the present invention have a pH between at or about 6.0 and at or about 8.0, more preferably at or about 6.8 to at or about 7.8, including about pH 7.0, pH 7.2, and 7.4. A preferred buffer is phosphate, with preferred counterions being sodium or potassium ions. Phosphate saline buffers are well known in the art, such as Dulbecco's Phosphate buffered saline. Buffer concentrations in total solution can vary between at or about 5 Mm, 9.5 Mm, 10 Mm, 50 Mm, 100 Mm, 150 Mm, 200 Mm, 250 Mm, and 500 Mm. Preferably the buffer concentration is at or about 10 Mm. Particularly preferred is a buffer 10 Mm in phosphate ions with a pH of 7.0.

Preferably, formulations of FSH analysed according to the method of the present invention have pH between at or about 6.0 and at or about 8.0, more preferably at or about 6.8 to at or about 7.8, including about pH 7.0, pH 7.2, and 7.4. A preferred buffer is phosphate, with preferred counterions being sodium or potassium ions.

Preferably formulations of mixtures of FSH and LH analysed according to the method of the present invention have pH between at or about 6.0 and at or about 9.0, more preferably at or about 6.8 to at or about 8.5, including about pH 7.0, Ph 8.0, and 8.2, most preferably at or about pH 8.0.

Preferably formulations of hCG analysed according to the method of the present invention have pH between at or about 6.0 and at or about 8.0, more preferably at or about 6.8 to at or about 7.8, including about pH 7.0, pH 7.2, and 7.4.

The protein sample is preferably a liquid formulation for single dose or multi-dose administration. Liquid formulations of the invention that are intended for multi-dose use preferably comprise a bacteriostatic, such as phenol, m-cresol, p-cresol, o-cresol, chlorocresol, benzyl alcohol, alkylparaben (methyl, ethyl, propyl, butyl and the like), thymol, benzalkonium chloride, benzethonium chloride, sodium dehydroacetate and thimerosal. Particularly preferred are phenol, benzyl alcohol and m-cresol, more preferred are phenol and m-cresol, most preferred is m-cresol. The bacteriostatic agent is used in an amount that will yield a concentration that is effective to maintain the formulation essentially bacteria free (suitable for injection) over the multi-dose injection period, which may be at or about 12 or 24 hours to at or about 12 or 14 days, preferably at or about 6 to at or about 12 days. The bacteriostatic is preferably present in a concentration of at or about 0.1% (mass bacteriostatic/mass of solvent) to at or about 2.0%, more preferably at or about 0.2% to at or about 1.0%. In the case of benzyl alcohol, particularly preferred is a concentration of 0.9%). In the case of phenol, particularly preferred is at or about 0.5%. In the case of m-cresol, particularly preferred is a concentration of at or about 0.3% (e.g. at or about 3 mg/ml in WFI).

Size Exclusion columns are well known to the person skilled in the art. They are chosen according to the respective protein and poloxamer in the sample. The gel of the column should be a polymer based matrix. A preferred column is a SE-HPLC column having the designation TSK G3000PW of TosoHaas Inc. The beads of the matrix have a particle size of 10 or 17 μm, a pore size of about 200 Å. The column is commercially available.

The detection step may be performed with any of the RI detection systems, which are known to a person skilled in the art.

It has been found that under more acididc conditions, the poloxamer could be separated more easily from the proteins.

Thus, the mobile phase used in the method according to the present invention is an aqueous solvent such as water or a buffered solution.

In a particular embodiment, the mobile phase is adjusted to a pH lower than 7, preferably lower than 3, more preferably between about 1.6-2.0 and most preferably between 1.9-2.0. In one embodiment the protein is a heterodimer, such as FSH, CG, LH or TSH. Under acidic conditions a heterodimer protein tends to decompose into its subunits which migrate more easily thus improving the separation and detection step (resolution). Acidic agents suitable to adjust the pH may be selected by the person skilled in the art. The most preferred acid is trifluoracetic acid (TFA).

Typically, the samples to be assessed are prepared and injected into the column. By having regard to the refractive index in the detection step of the method a chromatogram is obtained containing a peak area for the poloxamer as well as at least one further peak for the protein(s) and excipients. The assessment of the peak area allows the quantification of the poloxamer present in the analysed sample. The quantification is allowed since a standard curve with poloxamers is prepared (see Examples).

EXAMPLES

The present invention will now be illustrated by means of examples.

Figure 1:
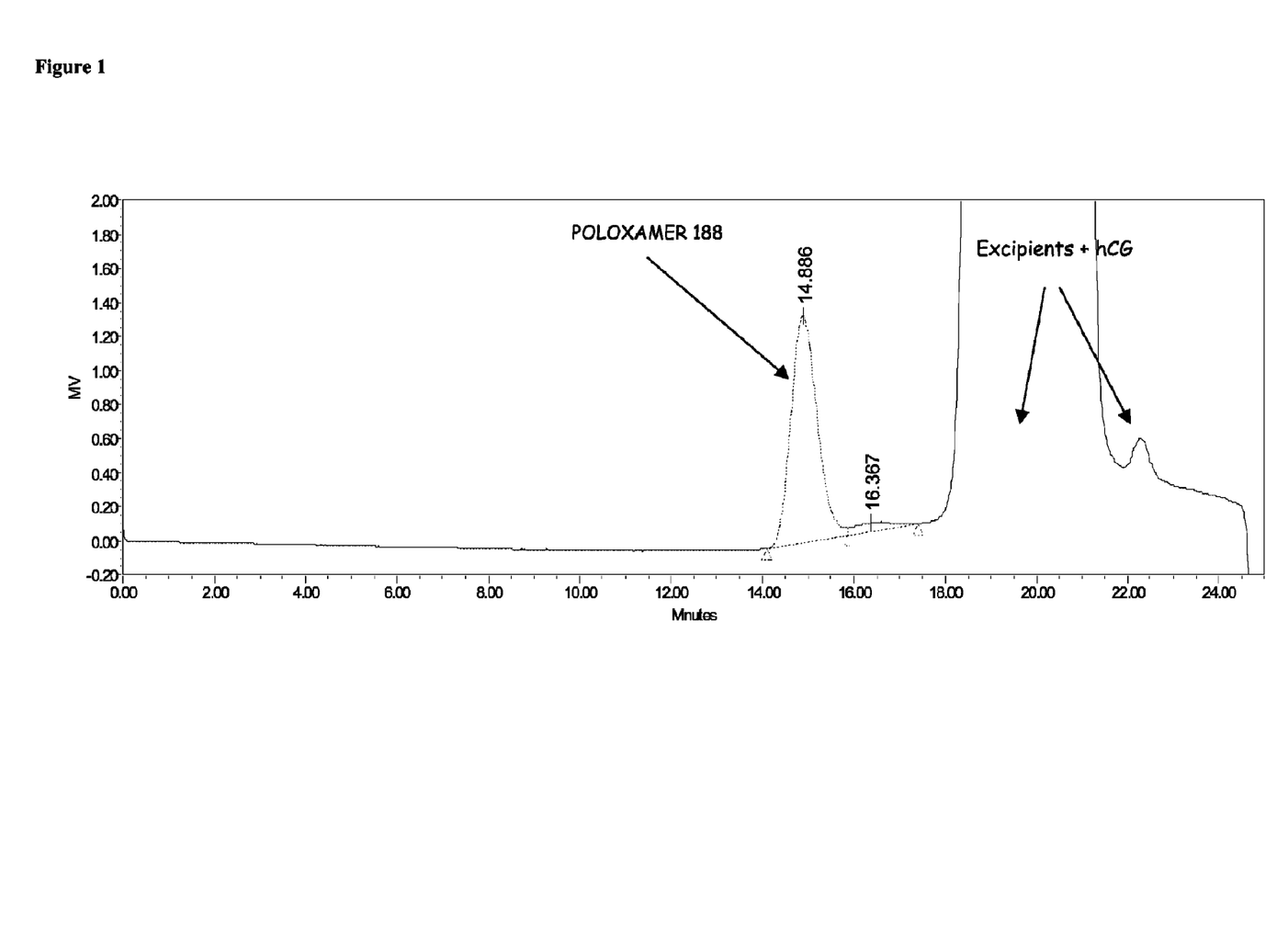

Example 1 cf FIG. 1

The purpose of this Example was to analyse the Poloxamer 188 concentration in a sample of the commercially available liquid hCG formulation Ovitrelle™ after 18 months of storage at room temperature. Thus, the stability of the liquid formulation in respect of Poloxamer 188 was assessed. The Poloxamer 188 concentration at the moment of preparation was about 100 mcg/ml. The protocol for the Poloxamer 188 quantitation in Ovitrelle™ was as follows.

The liquid injectable Ovitrelle™ contained the following ingredients Choriogonado-tropin alpha, mannitol, L-methionine, Poloxamer 188, phosphoric acid, NaOH and water.

1. Equipment and Materials

| | Provider |
|---|---|
| HPLC ALLIANCE mod.269 | Waters |
| RI detector mod. 2414 | Waters |
| Software Empower | Waters |
| Personal computer | IBM (or equiv.) |
| Poloxamer 188 - Lutrol F68 cod. 010293-1 | BASF |
| Trifluoracetic acid (TFA) cod.9470 (10 × 1 mL) | J. T. Baker |
| Analytical column TSKgel G3000 PWxl cod.08021 | TOSOH |
| D(−)Mannitol cod. 1.05983 | MERCK |
| L-Methionine cod. 1.05707 | MERCK |
| Ortho-Phosphoric acid 85% cod. 1.00573 | MERCK |
| Sodium Hydroxide 50% cod. 7067 | J. T. Baker |
| Ethanol gradient grade cod 1.11727 | MERCK |
| Ovitrelle syringes - hCG liquid formulation 250 mcg | SERONO |

2. Procedure 2.1 Eluent A (H$_2$O/TFA 0.5%)

To 950 ml of purified water, in a 1 litre graduated cylinder, 5 mL of trifluroracetic acid (TFA) were added and made up under stirring to 1000 ml. The pH of the eluent was between 1.7 and 1.9.

2.2 Eluent B (20% Ethanol)

To 750 ml of purified water, in a 1 litre graduated cylinder, 200 mL of Ethanol were added and made up under stirring to 1000 ml.

2.3 Wash Solution for Autosampler (10% Methanol)

To 850 ml of purified water, in a 1 litre graduated cylinder, 100 ml of methanol were added and made up under stirring to 1000 ml.

2.4 Seals Wash Solvent (5% Methanol)

To 900 ml of purified water, in a 1 litre graduated cylinder, 50 ml of methanol were added and made up under stirring to 1000 ml.

2.5 Standard Curve Dilution Solution (Liquid Formulation Without Poloxamer 188)

To 850 ml of purified water, in a 1 litre graduated cylinder, 54.6 g of D(−) Mannitol, 0,98 gr of Ortho-Phosphoric acid 85%, and 200 mcg of L-Methionine were added. The solution was brought to pH 7.0 by drop wise addition of 50% Sodium Hydroxide und made up to 1 ml. The solution was filtered by a 0.45 μm filter.

As an alternative, water may be used as standard curve dilution solution.

2.6 Concentrated Standard Curve Solution 200 mg of Poloxamer 188 were dissolved in 80 ml of purified water, in a 100 ml graduated cylinder, and made up to 100 ml. The standard curve was prepared based on the concentration expected in the samples to analyse. In this Example, a Poloxamer 188 concentration of about 100 mcg/ml was expected in the liquid injectable Ovitrelle™, the standard curve thus was in the range of 50-160 mcg/ml 3 Samples Preparation Blank 0.05 ml of standard curve dilution solution were injected.

Samples

All samples were tested without any pre-treatment and 0.05 ml were injected.

4. Operative Conditions 4.1. Instrument Set Up

The following solutions were connected to the HPLC lines:
Line A: Eluent A (H$_2$O/TFA 0.5%)
Line B: Eluent B (Ethanol 20%)

The lines A, and B were filled, the system was purged and rinsed at 2 mL/min flow rate for 3 minutes. The on line degasser, if present, was switched on.

Before the analysis the solenoid valve of the RI Detector of the flow was switched in the purge mode for at least 30 minute with line A. The purging of the flow cell was carried out to flush fresh mobile phase into the reference side of the cell.

Connection of the Column to the Instruments and Input of the Following Parameters:

| | |
|---|---|
| RI Detector temperature:: | 30° C. |
| Column temperature: | +20 ± 5° C. |
| Column flow rate | 0.5 ml/min |
| Elium flow rate: | 20 ml/min (in case the degasser is not in line) |
| Autosampler temperature: | +4° C. |
| Autosampler Loop | 200 mcl |
| Syringe size: | 250 mcl |
| Duration analysis: | 40 min |
| Next inject: | 5 min |

4.2 Column Equilibration

The column was flushed with eluent A, to equilibrate the column. The equilibration was completed when the baseline was stable.

4.3 Storage Column

After completion of the analysis the column was rinsed with at least 30 ml of purified water followed by 30 ml of 20% ethanol.

4.4 Determination of Poloxamer 188 Concentration in the Ovitrelle Samples

The model used to calculate the concentration of Poloxamer 188 in the Ovitrelle samples was the linear regression.

$$Y=a+bx$$

Wherein
Y=Total area of the Poloxamer 188
a=Intercept value
b=Slope value
x=Concentration of Poloxamer 188 in µg/injected ml.

The sample was integrated as shown in FIG. 1.

The intercept (a) and the slope (b) of the standard curve were calculated, the linear regression was calculated by the software Statgraphics plus.

The following formula was applied to calculate the concentration of Poloxamer 188.

$$C_{Poloxamer\,188} = \frac{y-a}{b} * FD \quad (FD = \text{Dilution factor}) \quad \text{Equation 1}$$

The solution of equation 1 gives the Poloxamer 188 concentration in each of the Ovitrelle samples expressed in µg/ml.

The Poloxamer concentration found in the samples of this Example (see FIG. 1) was about-94 mcg/ml.

Example 2

The purpose of this Example is to analyse the Poloxamer 188 concentration in a sample of the commercially available liquid hFSH formulation Gonal-F RFF Pen™ after 18 months of storage at room temperature. Thus, the stability of the liquid formulation in respect of Poloxamer 188 was to be assessed. The Poloxamer 188 concentration at the moment of preparation was about 100 mcg/ml. The protocol for the Poloxamer 188 quantitation in Gonal-F RFF Pen™ was identical as shown in Example 1 for Ovitrelle, with the exception that the column flow rate was 0.75 ml/min.

The poloxamer could be separated from the hFSH and was separately quantified.

Example 3

The purpose of this Example is to analyse the Poloxamer 188 concentration in a sample of the commercially available liquid hGH formulation Serostim™. The protocol was identical as in Example 2.

The poloxamer could be separated from the hGH and was separately quantified.

Example 4

The purpose of this Example was to analyse the Poloxamer 188 concentration in a sample of a liquid hIFN-beta formulation. The protocol was identical as in Example 2.

The poloxamer could be separated from the hIFN-beta and was separately quantified.

The invention claimed is:

1. A method for the quantitative determination of a poloxamer in a liquid protein sample comprising the steps of subjecting said sample to:
   a) a separation step using a size exclusion chromatography column;
   b) an elution step with a mobile phase adjusted to a pH below 3; and
   c) detecting the amount of poloxamer in said sample.

2. The method of claim 1, wherein the poloxamer is Poloxamer 188.

3. The method of claim 1, wherein the protein in said liquid protein sample has a molecular mass between 5-70 kDa.

4. The method of claim 3, wherein the protein has a molecular mass of between 20-70 kDa.

5. The method of claim 1, wherein the protein is a heterodimer protein.

6. The method of claim 5, wherein the protein is a gonadotropin selected from FSH, LH, hCG, TSH.

7. The method of claim 1, wherein the protein to be analysed is interferon beta or Growth Hormone (GH).

8. The method of claim 1, wherein the sample is an aqueous pharmaceutical composition containing FSH, LH, hCG, TSH, GH or interferon beta.

9. The method of claim 1, wherein the mobile phase is aqueous.

10. The method of claim 1, wherein the elution of the sample is performed with a mobile phase of acidic pH.

11. The method of claim 1, wherein the pH of the mobile phase is adjusted to about 1.9-2.0.

12. The method of claim 1, wherein the detection of poloxamer comprises analyzing the refractory index.

13. The method of claim 1, wherein the size exclusion column is a SE-HPLC column filled with a polymer based matrix containing beads.

14. The method of claim 13, wherein the beads of the matrix have a particle size of 10 or 17 μm.

15. The method of claim 13, wherein the beads of the matrix have a pore size of about 200 Å.

16. The method of claim 14, wherein the beads of the matrix have a pore size of about 200 Å.

* * * * *

UNITED STATES PATENT AND TRADEMARK OFFICE
CERTIFICATE OF CORRECTION

| | | |
|---|---|---|
| PATENT NO. | : 7,866,203 B2 | Page 1 of 1 |
| APPLICATION NO. | : 12/066799 | |
| DATED | : January 11, 2011 | |
| INVENTOR(S) | : Mara Rossi | |

It is certified that error appears in the above-identified patent and that said Letters Patent is hereby corrected as shown below:

Column 2,
Line 64, "to be analysed" should read --to being analysed--.

Column 3,
Lines 29-30, "a-I-antitrypsin" should read --a-l-antitrypsin--.
Line 40, "(MIP-I-alpha)" should read --(MIP-l-alpha)--.

Column 4,
Line 55, "used in QI" should read --used in OI--.
Line 60, "for QI and COH" should read --for OI and COH--.

Column 5,
Line 19, "a liquid FSH formulations is" should read --liquid FSH formulations are--.
Line 20, "33 μg/075 ml" should read --33 μg/0.75 ml--.
Line 56, "50-56]." should read --50-56.--.

Column 7,
Line 2, "systems may be consist" should read --systems may consist--.

Column 10,
Line 62, "Ph 8.0" should read --pH 8.0--.

Column 11,
Line 33, "more acididc" should read --more acidic--.

Signed and Sealed this
Twelfth Day of April, 2011

David J. Kappos
*Director of the United States Patent and Trademark Office*